(12) United States Patent
Huang et al.

(10) Patent No.: US 7,089,122 B2
(45) Date of Patent: Aug. 8, 2006

(54) METHOD FOR DETERMINING THE RESOLUTION OF BLOOD GLUCOSE

(76) Inventors: Yin-Chun Huang, 6F, No. 72-11, Lane 531, Sec. 1, Kuang-Fu Rd., Hsin-Chu City (TW); Kuo-Jeng Wang, 14, Kung-An St., Hsiao-Kang, Kaohsiung City (TW)

( * ) Notice: Subject to any disclaimer, the term of this patent is extended or adjusted under 35 U.S.C. 154(b) by 0 days.

(21) Appl. No.: 10/771,333

(22) Filed: Feb. 5, 2004

(65) Prior Publication Data

US 2004/0210401 A1 Oct. 21, 2004

(30) Foreign Application Priority Data

Apr. 4, 2003 (TW) .............................. 92107792 A

(51) Int. Cl.
*G01N 31/00* (2006.01)
(52) U.S. Cl. .................... 702/23; 204/403.02
(58) Field of Classification Search ............... 702/23; 204/403.02, 403.1, 403.01; 600/316, 322, 600/347; 514/12, 288; 435/193
See application file for complete search history.

(56) References Cited

U.S. PATENT DOCUMENTS

2002/0133064 A1* 9/2002 Ueno et al. ................. 600/316
2003/0150724 A1* 8/2003 Kawanaka et al. ..... 204/403.02

* cited by examiner

*Primary Examiner*—Michael Nghiem
*Assistant Examiner*—Xiuqin Sun
(74) *Attorney, Agent, or Firm*—Berkeley Law & Technology Group LLC

(57) ABSTRACT

The present invention provides a method for calculating the resolution of blood glucose which corresponding with the peak value of the rising curve. The average peak value is obtained from calculating the plurality of peak value, which determined after the pre-setting sampling time. Then, the average peak value is calculated with the resistance of the measuring circuit, reference resistance, and reference voltage to obtain the resolution of the blood glucose. Furthermore, the mapping table can be fabricated by the different height of maximum peak value and outputted voltage in different presetting sampling time, such that the resolution of blood glucose can be obtained in different outputted voltage values.

10 Claims, 4 Drawing Sheets

METHOD FOR DETERMINING THE RESOLUTION OF BLOOD GLUCOSE

BACKGROUND OF THE INVENTION

1. Field of the Invention

The present invention generally relates to a method for determining the resolution of blood glucose, and more particularly to a peak value of the rising curve method to determine the resolution of the blood glucose.

2. Description of the Prior Art

In the past, many systems have been developed for monitoring blood characteristics. For example, devices have been developed which are capable of determining such blood characteristics as blood oxygenation, blood glucose concentration. However, significant difficulties have been existed when attempting to specifically determine blood glucose resolution accurately using noninvasive blood monitoring systems such as by means of spectroscopic measurement.

The difficulty in determining blood glucose resolution accurately may be attributed to several causes. Firstly, within the bloodstream, the blood glucose is typically found in very low resolution (e.g., on the order of 100 to 1000 times lower than hemoglobin) so that such low resolutions are difficult to detect noninvasively, and require a very high signal-to noise ratio. Additionally, with spectroscopic methods, the optical characteristics of glucose are very similar to those of water that is found in a very high concentration within the blood. Thus, where optical monitoring systems are used, the optical characteristics of water tend to obscure the characteristics of optical signals due to glucose within the bloodstream.

Furthermore, dry phase reagent test strips incorporating enzyme-based compositions are used extensively in clinical laboratories, physicians' offices, hospitals and homes to measure the resolution of the compositions in the biological fluids. These strips have, for example, measured glucose, cholesterol, proteins, ketones, phenylalanine, or enzyme in blood, urine, or saliva. Measuring glucose resolution in samples of whole blood is a particularly common use. In fact, test strips have become an everyday necessity for many of the nation's several million people with diabetes.

Test strips are known that contain a testing reagent that turns a different shade of color, depending on the resolution of glucose in a blood sample that has been applied to the strips. The blood glucose resolution is measured by inserting a strip into a meter that is basically a reflectance photometer, which determines the resolution from the change in color caused by the reaction between the testing reagent and blood glucose. The testing reagent typically contains an enzyme, such as glucose oxidase, which is capable of oxidizing glucose to glucose acid lactone and hydrogen peroxide; an oxidizable dye; and a substance having peroxidative activity, which is capable of selectively catalyzing oxidation of the oxidizable dye in the presence of hydrogen peroxide.

SUMMARY OF THE INVENTION

It is an object of the present invention to provide a method for calculating the resolution of blood glucose by the relationship between the rising curve and the blood glucose resolution. The resolution of the blood glucose could be obtained from calculating these known values which including the slope on the peak point, resistance, reference resistance reference voltage, and the average peak value obtained from calculating the plurality of peak value after the pre-setting sampling time.

It is still an object of the present invention to obtain the maximum of the peak value by using the property of the first differential of the peak value being greater than zero.

It is yet object of the present invention to obtain the different height of the peak value after the pre-setting different sampling time and take them to make a mapping table.

It is a further object of the present invention to get the resolution of blood glucose concentration according to the different voltage on the mapping table.

According to the above-mentioned objects, the present invention provides a method of determining the resolution of the blood glucose corresponding with the peak value of the rising curve. The peak value of the rising curve is the basis for determining the blood glucose resolution in the present invention. The resolution of the blood glucose could be obtained from calculating the given values, which including the slope on the peak point, resistance of the determining circuit, reference resistance and reference voltage and the average peak value obtained from calculating the plurality of peak value after the pre-setting sampling time. Furthermore, the mapping table can be created by recording the variable peak value according to the variable pre-setting sampling time, and correspond to the mapping table to obtain the different resolution of blood glucose under the different outputted voltage.

BRIEF DESCRIPTION OF DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE INVENTION

An appropriate and preferred embodiment will now be described in the section. It should be noted, however, that this embodiment is merely an example and can be variously modified without departing from the scope of the present invention. The present invention provides a performance method described as follow:

Firstly, the blood glucose solution is placed on the test strip with the test reagent or catalyst such as enzyme, wherein the test reagent will reacted with the blood glucose solution to generate the oxidation reduction reaction to generate an analog source. Then, the analog source is inputted into a determining circuit of the determining meter to transfer into a treatment device to transfer the digital signal from the analog source, and then outputting the digital signal to a display apparatus.

Figure 1:
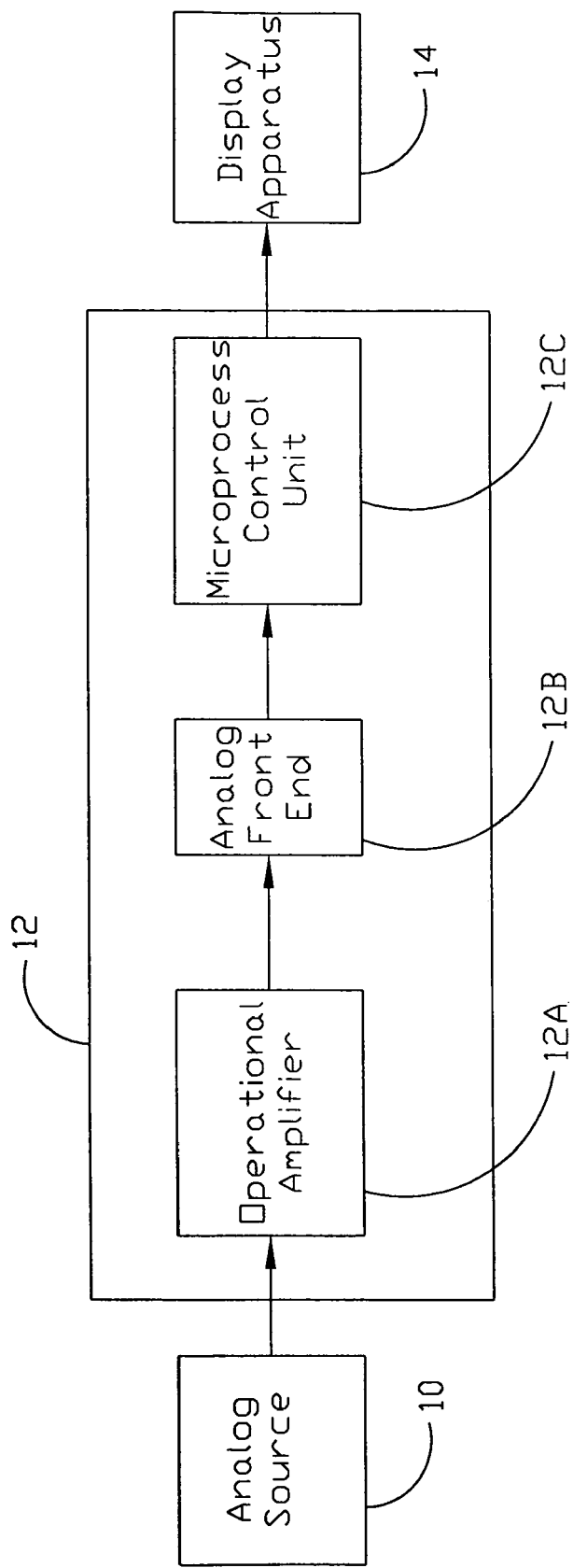
FIG. 1 is a schematic diagram showing the peak value to determine the resolution of the blood glucose in accordance with a method disclosed herein.

Referring to FIG. 1, a schematic diagram showing the steps of the method to determine the blood glucose resolution by utilizing the peak value. Firstly, with reference number 0 denotes the analog source, which generated from the chemical reaction between the blood glucose solution and the test reagent with the enzyme such as catalyst; then, analog source is inputted into a treatment device 12 to transfer the analog source and is outputted into a display apparatus 14, wherein the treatment device comprises an OP (operational amplifier 12A) with at least one resistor, when the blood glucose resolution is getting higher, the resistance is also getting higher. Then, the analog source is transferred into the AFE (analog front end) 12B. The analog source is transferred into the digital signal when the analog source s transferred to the AFE 12B, wherein the AFE 12B can be ADC (analog to digital converting system). Next, the digital signal is communicated into the MCU (microprocessor control unit) 12C to treat. Thereafter, the digital signal is outputted in the display apparatus 14. The diagram in the display apparatus 14 is a curve diagram.

Figure 2:
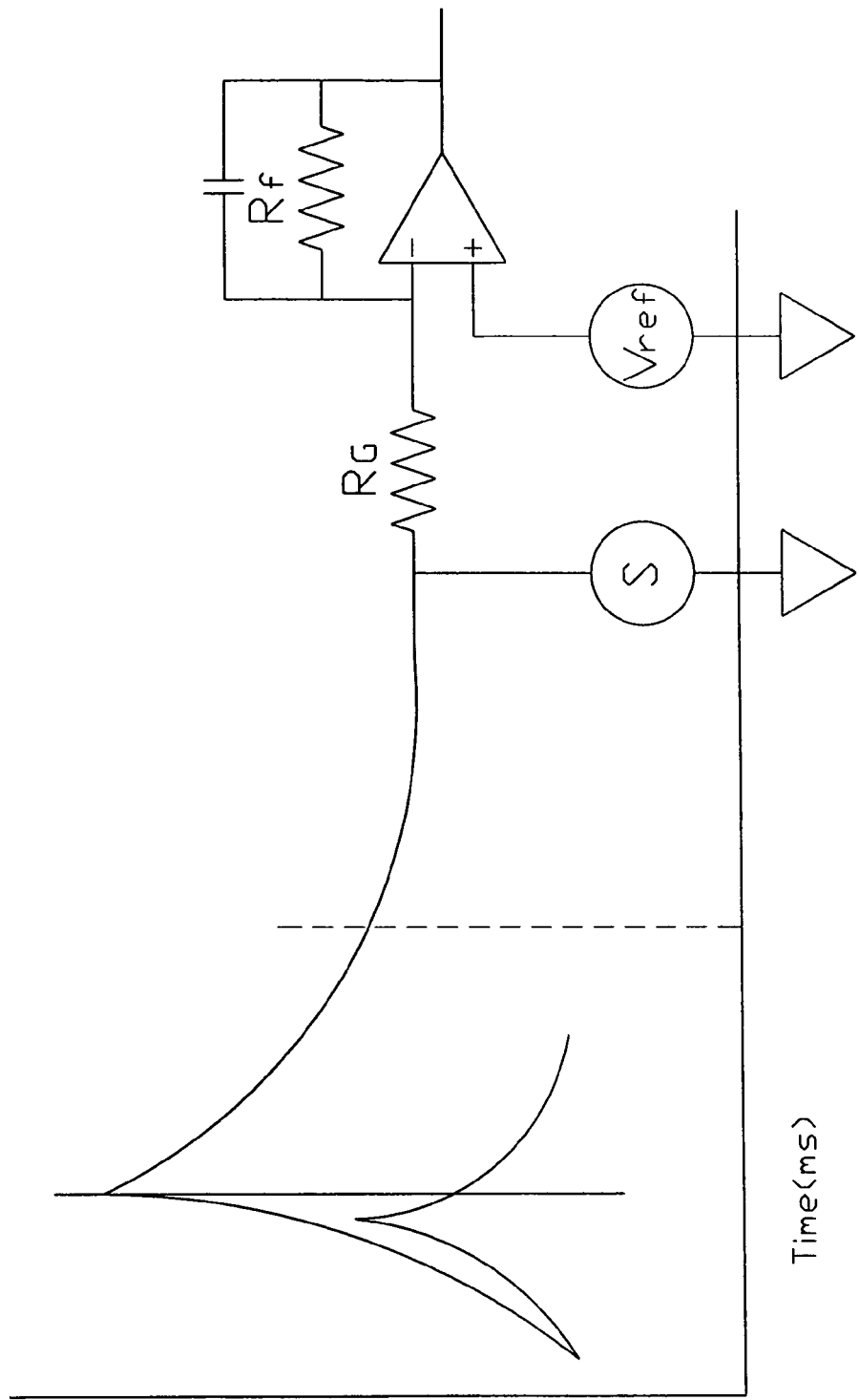
FIG. 2 is a schematic diagram showing the relationship between the the rising curve and the operation amplifier in accordance with a method disclosed herein.

FIG. 2 is schematic diagram illustrating the relationship between the rising curve of blood glucose resolution and the operational amplifier. After the blood glucose solution reacting with the test reagent to product the analog signal source, the height of the curve is determined on the blood glucose concentration and the resistance, the resistance increasing with the increase of the blood glucose concentration. After the analog signal source being transferred into operation amplifier, the analog signal source will be transformed and transferred out as the outputted voltage ($V_{out}$) from these known values, the slope on the peak point, the resistance ($R_G$) in the operation amplifier, the reference resistance ($R_f$) and the reference voltage ($V_{ref}$).

Figure 3:
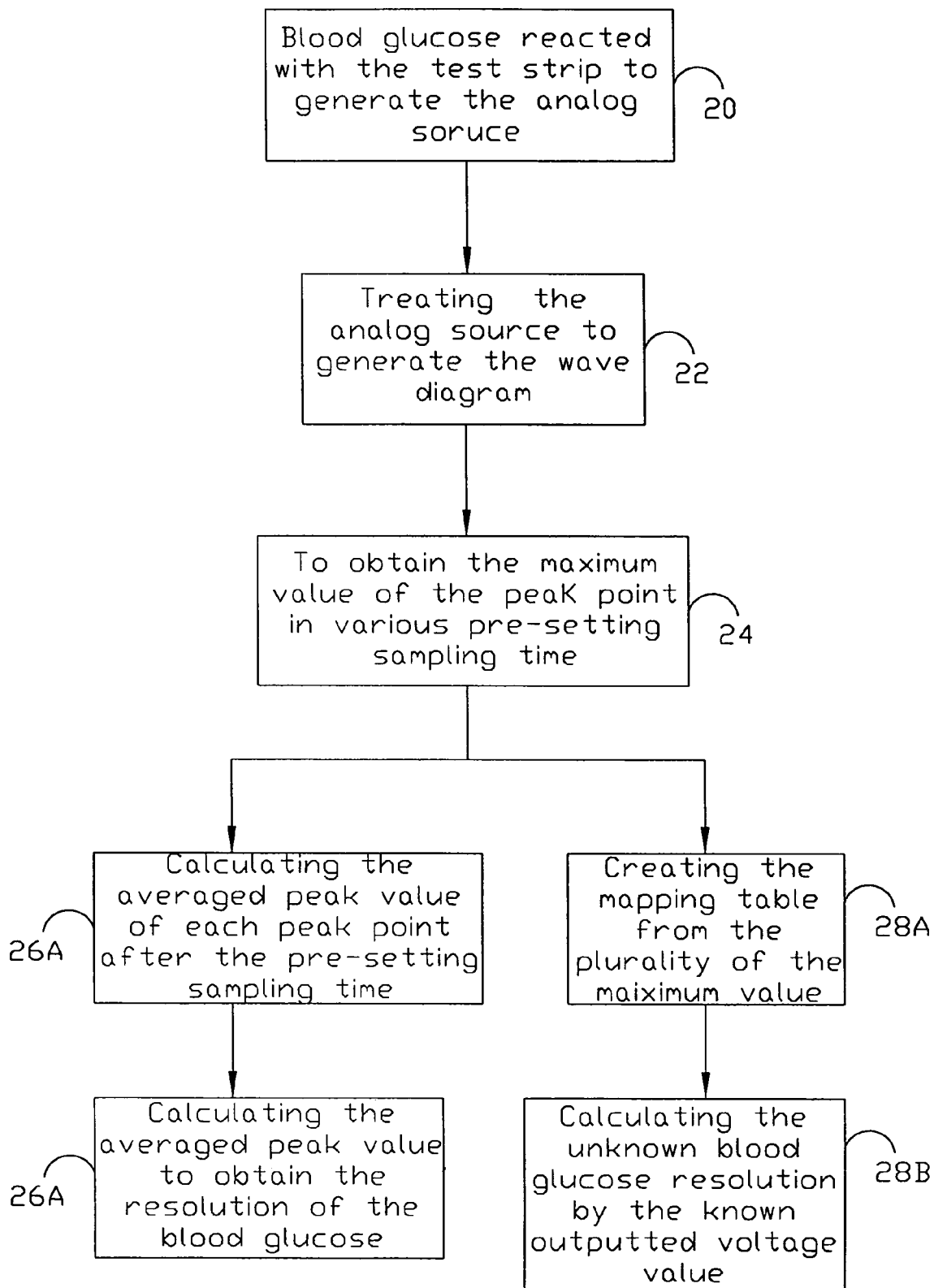
FIG. 3 is a flow chart showing the steps for determining the resolution of the blood glucose by using the peak value in accordance with a method disclosed herein.

FIG. 3 is schematic diagram illustrating the flow steps of getting the resolution of the blood glucose concentration by the peak value. In this figure, step 20 means that the blood glucose solution has a chemical reaction by reacting with the catalyst to product the analog signal source, the chemical reaction may be an oxidation reduction reaction. Then, step 22 treat the analog signal source and product a wave diagram. And then, at step 24, getting the maximum value of the wave diagram after the pre-setting sampling time. In the firstly preferred embodiment of the present invention, the average peak value could be obtained at step 26A by calculating the plurality of peak value after the pre-setting sampling time. And at step 26B, the method would get the resolution of the blood glucose concentration by the average peak value. Furthermore, in the other preferred embodiment, at step 28A, the method of the present invention could make the plurality of peak value be a mapping table which shows the relationship between the blood glucose concentration and the outputted voltage. And, at step 28B, the method of the present invention could calculate the resolution of the blood glucose concentration by obtaining the outputted voltage value of an unknown blood glucose solution and looking into the mapping table.

Figure 4:
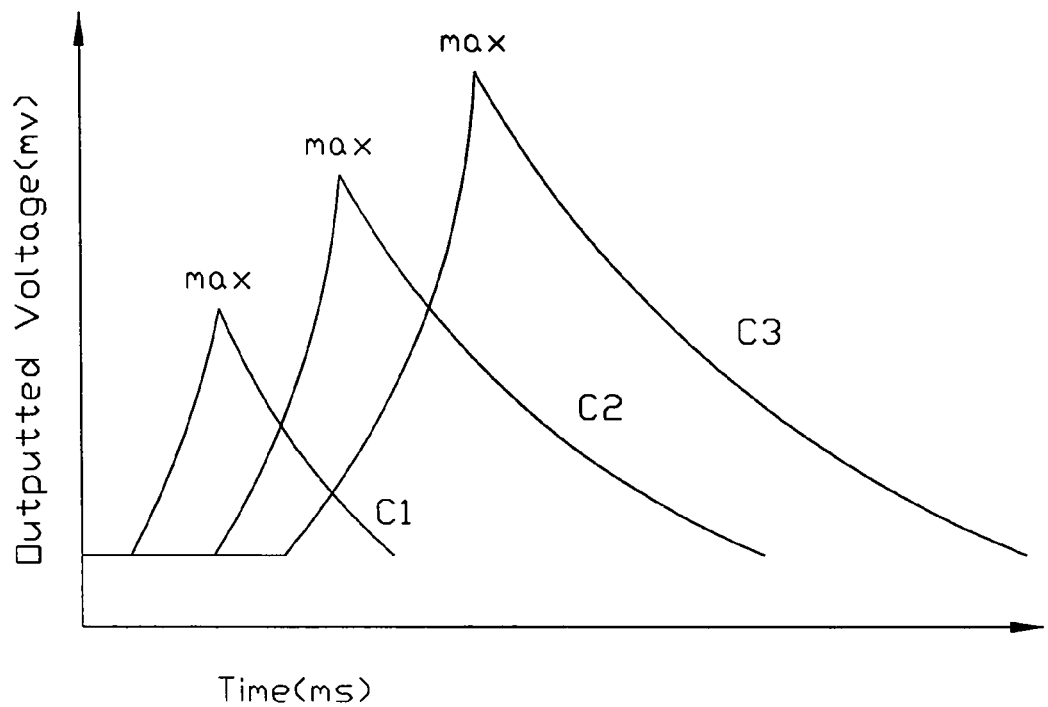
FIG. 4 is a schematic diagram showing the rising curve of the blood glucose resolution in accordance with a method disclosed herein.

FIG. 4 is schematic diagram illustrating the rising curve of the blood glucose concentration. From the FIG. 4, the present invention will get the peak value after the pre-setting sampling time from the property of the first differential is larger than zero, $y(t_1)-y(t_0)>0$, which is the difference between the first time ($t_1$) and the initial time ($t_0$) and it is larger than zero. With reference to the FIG. 4, in the firstly preferred embodiment of the present invention, the average peak value could be obtained by adding and averaging the plurality of peak value after the pre-setting sampling time. From calculating the average peak value, the slope of the peak point, resistance, reference resistance and reference voltage, the method can get the resolution of the blood glucose concentration.

Figure 5:
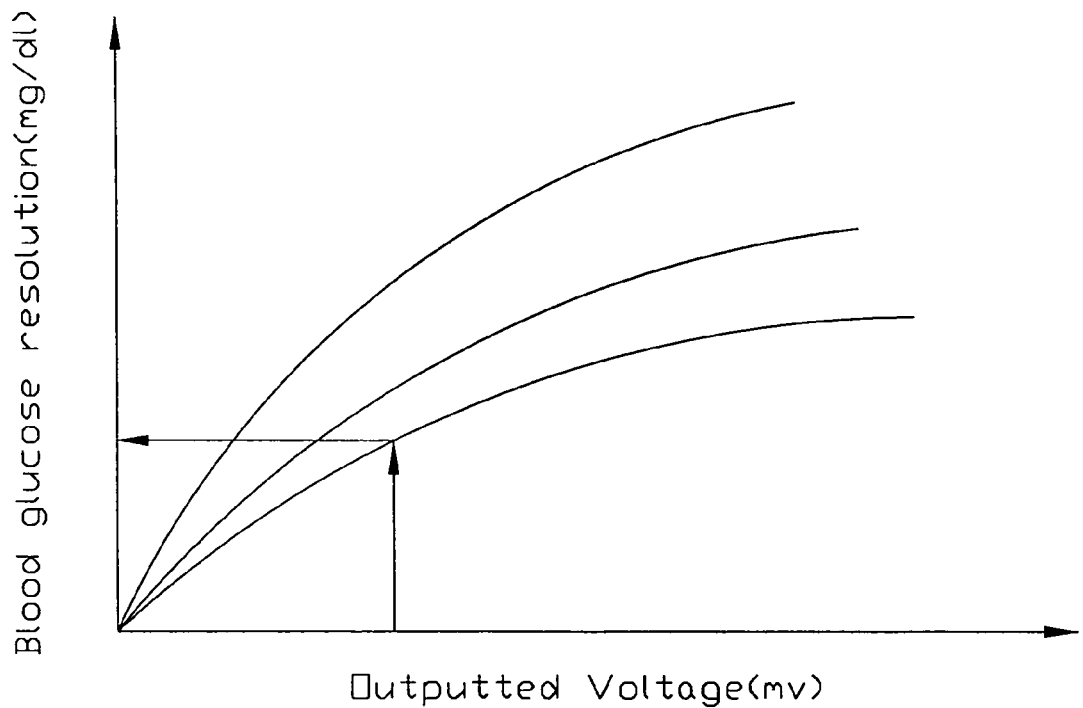
FIG. 5 is a schematic diagram showing the rising curves for the different blood glucose resolution solution in accordance with a method disclosed herein.

FIG. 5 is schematic diagram illustrating the rising curves of the different concentrations of the blood glucose solutions. In the FIG. 5, curves C1, C2 and C3 mean the different blood glucose concentrations. As the same, from the property of the first differential is larger than zero, the method of the present invention get the peak value of the curve and make a mapping table of the outputted voltage and blood glucose concentration from the plurality of peak value. Therefore, the method of calculating the real resolution of the blood glucose concentration is to obtain the outputted voltage value of an unknown blood glucose solution and look into the mapping table.

While this invention has been described with reference to illustrative embodiments, the description is not intended being construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for determining a resolution of blood glucose, comprising:
   obtaining an analog signal source from a blood glucose solution being applied to an amplifier circuit which includes a reference resistance;
   transforming said analog signal source into a digital signal;
   transmitting said digital signal with a rising curve to obtain an approximate local maximum value of said rising curve;
   determining said resolution of blood glucose according to said approximate local maximum value; and
   determining an average peak value of a plurality of said approximate local maximum values after a pre-setting sampling time.

2. A method for determining a resolution of blood glucose, comprising:
   obtaining an analog signal source from a blood glucose solution being applied to an amplifier circuit which includes a reference resistance;
   transforming said analog signal source into a digital signal;
   transmitting said digital signal with a rising curve to obtain an approximate local maximum value of said rising curve;
   determining said resolution of blood glucose according to said approximate local maximum value; and
   providing a mapping table of an outputted voltage and a plurality of approximate local maximum values from a plurality of said rising curves.

3. A method for determining the resolution of blood glucose, comprising:
   providing a blood glucose solution for reaction on a test strip to produce an analog signal source;
   transmitting said analog signal source into a measuring circuit;
   transforming said analog signal source into a digital signal;
   outputting said digital signal with a rising curve;
   determining an average peak value at an approximate local maximum point of said rising curve after a pre-setting sampling time; and determining said resolution of blood glucose according to said average peak value.

4. The method according to claim 3, wherein said test strip includes a catalyst.

5. The method according to claim 3, and further comprising:
producing said analog signal source at least in part in response to an oxidation reduction reaction.

6. The method according to claim 3, wherein said measuring circuit includes a reference resistance.

7. The method according to claim 3, wherein said transforming said analog signal source includes transmitting said analog signal source through an analog front end (AFE).

8. The method according to claim 3, and further comprising determining an approximate local maximum value of said rising curve.

9. The method according to claim 8, wherein said approximate local maximum value being a difference between a first time ($t_1$) and an initial time ($t_0$) and said difference being larger than zero.

10. The method according to claim 6, wherein said resolution of blood glucose is determined at least in part based on said reference resistance.

* * * * *